US006837877B2

(12) United States Patent
Zurcher

(10) Patent No.: US 6,837,877 B2
(45) Date of Patent: Jan. 4, 2005

(54) SAFETY SHIELD ASSEMBLY

(75) Inventor: Robert Zurcher, Little Falls, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 142 days.

(21) Appl. No.: 09/922,620

(22) Filed: Aug. 6, 2001

(65) Prior Publication Data

US 2003/0229320 A2 Dec. 11, 2003

Related U.S. Application Data

(63) Continuation-in-part of application No. 09/378,976, filed on Aug. 23, 1999, now Pat. No. 6,440,104.

(51) Int. Cl.[7] .............................................. A61M 5/00
(52) U.S. Cl. ...................... 604/263; 128/919; 600/573
(58) Field of Search ................................ 604/187, 192, 604/198, 263, 164.01, 165.03, 174, 179; 128/919; 600/573, 576

(56) References Cited

U.S. PATENT DOCUMENTS

| | | | |
|---|---|---|---|
| 2,408,323 A | 9/1946 | Lockhart | |
| 3,306,290 A | 2/1967 | Weltman | |
| 3,658,061 A | 4/1972 | Hall | |
| 4,085,737 A | 4/1978 | Bordow | |
| 4,743,265 A | * 5/1988 | Whitehouse et al. | ....... 604/161 |
| 4,747,836 A | 5/1988 | Luther | |
| 4,834,715 A | 5/1989 | Hanifl | |
| 4,886,503 A | 12/1989 | Miller | |
| 4,944,397 A | 7/1990 | Miller | |
| 4,950,249 A | 8/1990 | Jagger | |
| 4,966,591 A | 10/1990 | Yuen | |
| 4,982,842 A | 1/1991 | Hollister | |
| 5,055,102 A | 10/1991 | Sitnik | |
| 5,084,027 A | 1/1992 | Bernard | |
| 5,116,325 A | 5/1992 | Paterson | |
| 5,135,509 A | 8/1992 | Olliffe | |
| 5,139,489 A | 8/1992 | Hollister | |
| 5,147,319 A | * 9/1992 | Ishikawa et al. | ............ 604/174 |
| 5,151,089 A | 9/1992 | Kirk, III | |
| 5,154,285 A | 10/1992 | Hollister | |
| 5,188,611 A | 2/1993 | Orgain | |
| 5,192,275 A | * 3/1993 | Burns | .......................... 604/263 |
| 5,207,653 A | 5/1993 | Janjua | |
| 5,312,367 A | 5/1994 | Nathan | |
| 5,423,765 A | 6/1995 | Hollister | |
| 5,437,648 A | 8/1995 | Graves | |
| 5,445,619 A | 8/1995 | Burns | |
| 5,490,841 A | 2/1996 | Landis | |
| 5,509,907 A | 4/1996 | Bevilacqua | |
| 5,584,816 A | 12/1996 | Gyure | |
| 5,599,318 A | 2/1997 | Sweeney et al. | |

(List continued on next page.)

FOREIGN PATENT DOCUMENTS

| | | | |
|---|---|---|---|
| EP | 460821 A1 | | 5/1991 |
| EP | 566631 B1 | | 12/1991 |
| EP | 520930 A1 | | 5/1992 |
| EP | 0623358 A2 | | 11/1994 |
| EP | 0 997 159 | * | 8/1999 |
| EP | 1 285 677 | * | 6/2002 |
| WO | 93/1299 | | 7/1993 |

*Primary Examiner*—LoAn H. Thanh

(57) ABSTRACT

An intravenous (IV) infusion and/or blood collection assembly including a safety shield. The shield is particularly useful with winged needle assemblies. The shield is pivotally secured to the winged needle assembly to enable pivotal movement from a position away from the needle to a position enclosing the needle. The shield is lockable in a position over the used needle to prevent the user from contacting the used needle.

5 Claims, 2 Drawing Sheets

U.S. PATENT DOCUMENTS

| | | |
|---|---|---|
| 5,615,771 A | 4/1997 | Hollister |
| 5,632,732 A | 5/1997 | Szabo |
| 5,643,219 A | 7/1997 | Burns |
| 5,649,622 A | 7/1997 | Hollister |
| 5,662,617 A | 9/1997 | Odell |
| 5,665,075 A | 9/1997 | Gyure |
| 5,669,889 A | 9/1997 | Gyure |
| 5,681,295 A | 10/1997 | Gyure |
| 5,807,351 A | 9/1998 | Kashmer |
| 5,868,716 A | 2/1999 | Sweeney et al. |
| 6,309,376 B1 | 10/2001 | Alesi |
| 2001/0008963 A1 | 7/2001 | Alesi |

\* cited by examiner

SAFETY SHIELD ASSEMBLY

RELATED APPLICATIONS

This application is a continuation-in-part of application Ser. No. 09/378,976 filed on Aug. 23, 1999 now U.S. Pat. No. 6,440,104.

BACKGROUND OF THE INVENTION

1. Field of the Invention

The present invention relates to intravenous infusion and blood collection assemblies and more particularly, intravenous infusion and blood collection assemblies with a safety shield. In particular, the present invention relates to a safety device for winged needle assemblies.

2. Description of Related Art

A conventional intravenous (IV) infusion or blood collection assembly usually includes an elongated small gauged plastic flexible tubing material having at one end thereof a disposable needle and a body or housing for holding the needle. Usually, the needle body is adhered to one end of the flexible tube by friction. The needle body includes wings extending on either side for the phlebotomist or user to grasp or hold the needle body for inserting the needle into a patient. Additionally, wings enable improved angles of penetration of the needle. Such assemblies may be used for infusing medication into a patient or for collecting blood from a patient. Generally, at the end of a flexible tube opposite the needle body is a female luer connection for connecting supplies of fluid to be infused or for connecting some sort of apparatus for collecting blood, as required.

After the needle of the assembly has been withdrawn from the patient, protection of the used needle tip becomes important. With concern about infection, transmission of AIDS, hepatitis and similar blood borne pathogens, methods and devices to enclose the used disposable needle have become very important and in great demand.

As a result, numerous devices have been developed for shielding needles after use. These structures usually involve some sort of shield arrangement, which moves in place over the used needle, once it has been removed from the patient. Current shielding structures for IV infusion or blood collection assemblies are often cumbersome, expensive and complex. In fact, the wings of these assemblies may interfere with the closure of some of the current shielding structures. Additionally, some of the current shielding structures may interfere with the normal and accepted procedure of one handed needle placement techniques or are so complex that they preclude use of the device in certain procedures or with certain devices and/or assemblies.

With the increased emphasis on concerns about the proper disposal of used needles, a special need exists for an improved assembly that will have an effective mechanism for covering the used needle without interfering with the accepted one hand needle placement techniques. The shielding assembly would effectively cover and lock in place over a used needle and substantially prevent the used needle for making contact outside that covering.

Accordingly, there exists a need for a safety shield assembly for an IV infusion or blood collection assembly that is easily manufactured, simple to use with one hand, capable of being safely disposed, and does not interfere with normal practices of use. Additionally, there is a need for a IV infusion and/or blood collection assembly that has tactile features whereby the user may be deterred from contacting the needle but is able to easily orient the needle with the patient and easily actuate and engage the shield assembly. Moreover, there is a need for an assembly that is not bulky or complex, has means for minimizing user exposure to residual fluid leaking from the needle and provides minimal exposure time to the user because the needle shield is able to be immediately initiated by the user after the needle is withdrawn from the patient.

SUMMARY OF THE INVENTION

The present invention provides an intravenous (IV) infusion and blood collection assembly with an easily maneuverable needle shield that overcomes the disadvantages of current blood collection assemblies with safety shields.

In particular, the present invention provides a safety shield that does not interfere with the wings present on a needle assembly and does not interfere with normal practices of needle use. Further, the assembly of the presentation is easy to use, is cost efficient to manufacture, and provides increased safety to the user.

The present invention provides a shield intravenous infusion or blood collection assembly. The assembly includes an elongate needle, a length of tubing, and an elongate housing supporting the needle at one end and the tubing at the other end in fluid communication. The housing includes a pair of oppositely directed outwardly extended wings. The assembly further includes a shield pivotally secured to the housing for pivotal movement from a position away from the needle to a position enclosing the needle.

As shown in the preferred embodiment, the shield of the present invention includes a proximal end, a distal end, a pair of opposed sidewalls and a top surface thereby defining an elongated recess extending from the distal end to the proximal end for housing the needle therein. The shield may be mounted to the housing by use of clips which may be secured to the housing. The shield is pivotally secured to the clips. The shield sidewalls include opposed inwardly directed protrusions adjacent the proximal end of the shield for engaging the clips or housing when the shield is in the enclosed position over the needle, locking the shield in the enclosed position. The sidewalls also have at least one inwardly directed protrusion adjacent the distal end of the recess of the shield. The distal protrusion is deflectable by the needle when the needle enters the elongated recess and the distal protrusion returnable to its undeflected position to permanently lock the needle within the shield.

DETAILED DESCRIPTION

Figure 1:
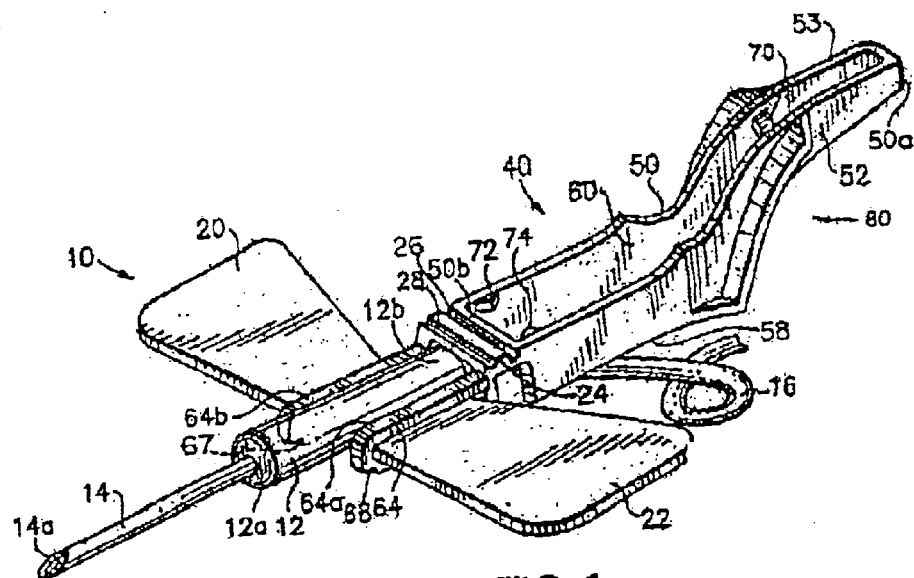
FIG. 1 is a perspective view of the safety shield assembly of the present invention as connected to a blood infusion set, shown in the open.

While this invention is satisfied by embodiments in many different forms, there is shown in the drawings and will herein be described in detail preferred embodiments of the invention, with the understanding that the present disclosure is to be considered as exemplary of the principles of the invention and is not intended to limit the invention to the embodiments illustrated. Various other modifications will be apparent to and readily made by those skilled in the art without departing from the scope and spirit of the invention. The scope of the invention will be measured by the appended claims and their equivalents.

A convention adopted for this disclosure is that the term "distal" or "needle end" refers to the direction away from the user or practitioner and the term "proximal" or "non-patient end" refers to the direction toward the user. Additionally, as used throughout this disclosure, the term "needle" is intended to encompass the broad range of penetration fluid delivery elements known in the art, including a pointed or sharpened needle cannulae as well as a blunt ended cannulae. It will also include cannulae supplied separately from and thereafter attached to the medical delivery instrument, as well as cannulae formed with during manufacture or otherwise considered integral with the medical delivery instrument.

The present invention provides a needle assembly that includes a safety shield to protect the user from contacting a used needle. Specifically, the present invention provides for an intravenous (IV) infusion or blood collection assembly having a safety shield. The present invention is extremely easy to use and requires only one-handed operation versus two-handed operation as required by some existing products. The use of this invention is intuitive, so it will not require retraining of users. The needle assembly of the present invention provides for safely handling such devices by reducing exposure to the used needle piece of the assembly as well as reducing the risk of accidental needle sticks while an operator is covering the used needle. Additionally, the present invention provides a safety shield that does not interfere with the wings present on a needle assembly. Thus, the presence of the wings does not inhibit the movement and operation of the safety shield.

Figure 2:
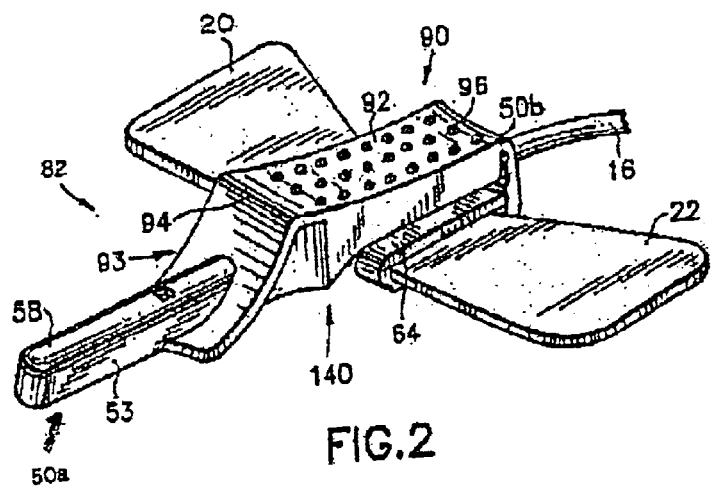
FIG. 2 is a perspective view of the safety shield assembly of FIG. 1 shown in the forward, locked position.

One embodiment of the intravenous (IV) infusion assembly 10 of the present invention is shown in FIGS. 1 and 2. The winged IV infusion assembly 10 of the present invention includes an elongate housing 12, an elongate needle 14 that extends distally from a distal end 12*a* of the housing 12 and a length of tubing 16 that extends proximally from a proximal end 12*b* of the housing 12. The needle 14 and the tubing 16 extend outwardly from the housing 12 and are connected in fluid communication by the housing 12. The housing 12 has a pair of oppositely directed wings 20 and 22 extending outwardly from the housing 12. Housing 12, needle 14 and tubing 16 are of conventional constitution and are typically used for blood collection and IV infusion.

The wings 20 and 22 of the assembly 10 are projected outwardly from the housing 12 and may be flexible or rigid. Generally, the wings 20 and 22 are formed as an integral structure with housing 12 with each wing flexing at the boundary therewith. The wings 20 and 22 may be attached to the distal end 12*a* or proximal end 12*b* of the outer sides of the housing 12. Wings 20 and 22 are used in the same way as wings on a conventional IV infusion assembly. Wings 20 and 22 provide the user with better gripping means so that the needle placement is easier. The wings 20 and 22 aid in positioning the needle at a desirable angle with respect to insertion, which reduces the incidence of penetration of the needle 14 through the far wall of the vein. Additionally, the wings 20 and 22 inhibit the assembly from rotating or moving while the needle 14 is in the patient. Thus, wings 20 and 22 protect the patient from injury that may result from needle movements while the needle is in the patient.

Flexible tubing 16 extends from the proximal end 12*b* of the housing 12 and, as is conventionally known, is used to allow the user to connect assembly 10 to supplies of infusion liquids or for the return of collected blood if the arrangement is being used to collect blood.

In order to cover the needle 14 once it has been withdrawn from the patient, the present invention provides a safety shield assembly 40. Safety shield assembly 40 includes a safety shield 50 and a mounting clip 64 for securing the safety shield to the housing 12. Safety shield assembly 40 is typically formed of molded plastic and is preferably integrally formed as described in detail hereinbelow. The shield 50 of present invention includes a proximal end 50*b*, a distal end 50*a*, a pair of opposed sidewalls 52 and 53 and a top surface 58 thereby defining an elongated recess 60 extending from the distal end 50*a* to the proximal end 50*b* for housing the needle 14 therein.

The shield 50 pivotally moves about a hinge 24 to a position 80 away from the needle so that the shield does not interfere with the use of the needle. After the needle is used, the shield 50 is easily moved with a single hand to a position 82 enclosing the needle.

Top finger guide 90 area has a ramp 92 that extends slightly on an upwardly slope from the proximal side of the shield 50*b* to a shoulder 94. From shoulder 94 extends a second ramp 93 which slopes downwardly towards top surface of the shield 58. Most preferably, first ramp 92 has touch bumps 96, which provide a tactile and visual guide to alert the user that the user's finger has contacted the shield 50 and that the shield is in a defined or controlled position. The touch bumps 96 may be any configuration so long as they extend and are distinct from the top finger guide area. The touch bumps 96 may also be of a distinguishing color as compared to the top finger guide area 90 or shield 50.

The shield sidewalls 52 and 53 include opposed inwardly directed proximal protrusions 72 and 74 adjacent to the proximal end 50*b* of the shield 50 that engage the clip 64 when the safety shield 50 is in the enclosed position 80 over the needle 14. As shown in FIG. 1, the hinge axis 24 is located on the tubing side or proximal side of the housing 12*a* and the proximal protrusions 72 and 74 engage the clip 64 as the shield is lowered over the needle 14.

One sidewall 52 or 53 has an inwardly directed distal protrusion 70 adjacent to the distal end of the shield 50*a* that are useful for engaging the needle when the shield is in the closed position. It is also contemplated that more than one distal protrusion 70 may be located on sidewall 52 or 53. The distal protrusion 70 provides a second locking mechanism to keep the shield 50 in its closed position 80 over the needle 14. The distal protrusion 70 engages the needle 14 as the shield 50 is moved into position 80 enclosing the needle. The protrusion 70 is deflectably moved by the needle 14 as the shield 50 is closed over the needle 14. Once the needle 14 passes the end of the protrusion 70, the protrusion returns to its original undeflected position and the needle is permanently locked in recess area 60 of the shield 50.

Thus, the shield of the present invention locks the needle in the elongate recess by a double locking mechanism which securely and permanently locks the shield over the needle. Alternative locking and closure mechanisms for the protective shield may be used. The locking assemblies desirably provide a secure locking position of the shield relative to the needle so as to prevent a used needle from being exposed against inadvertent tough contact by the user.

The shield assembly 40 is mounted to the infusion needle assembly 10 by clip 64. Clip 64 is arranged about wings 20 and 22 adjacent housing 12 and includes two spaced apart clip extensions 64*a* and 64*b* which surround wings 20 and 22 adjacent housing 12. The clip extensions 64a and 64b are flexible members, which may be used to snap clip 64 onto housing 12 in conventional fashion. In that regard, clip extensions 64a and 64b each have a living hinge 67 and 68, respectively, which enables them to be positionable about the wings 20 and 22 adjacent to the housing 12. The clip 64 and shield 50 may be integrally formed as a unitary article of manufacture and having a hinge axis 24 therebetween. Useful types of structures forming hinge axis 24 include mechanical hinges and various linkages, living hinges or combinations of hinges and linkages.

Desirably, the joint is a living hinge. A living hinge is most preferably a pair of spaced apart hinge elements 26 and 28 that form a double "living hinge." A "living hinge" may be formed when the shield and mounting are formed by injection molding a thermoplastic resin. The "living hinge" in the injection molded article is produced by having a reduced thickness of the plastic resin relative to its surrounding area and the molded part is flexed at the area of reduced thickness relative to its surrounding area. Then, the molded part is flexed at the area of the reduced thickness immediately after the part is removed from the injection molding tool and the area of reduced thickness functions as a hinge because the polymer molecules of the resin are oriented by the flexion. If the article is not flexed immediately, the ability to form a hinge is lost, hence the term "living hinge." Thus, the shield and clips in the present invention are preferably manufactured with a strip including an area of reduced thickness which is formed into a living hinge when the article is freshly removed from the mold tool.

Although a living hinge is the preferred hinge mechanism, any type of hinge axis that is capable of moving the shield about the housing of the assembly is suitable for use with the present invention. Acceptable hinges include mechanical hinges and various linkages, living hinges or combinations of hinges and linkages. For instance, the shield may be connected to the housing by a hanging bar and hook arm whereby the hanging bar engages with the hook arm so that the shield may be pivoted with respect to the collar and the shield is easily movable into several positions. Thus, the shield may be connected to the housing by an interference fit between the hanger bar and the hook arm.

The needle 14 desirably has an upwardly facing beveled distal end 14a for easy intravenous access. The assemblies of the present invention desirably have the shield 50 and wings 20 and 22 connected in alignment with the upwardly facing bevel end 14a of the needle 14. Alignment of the shield 50, wings 20 and 22 and needle 14 with the upwardly facing distal bevel end 14a of the needle 14 makes it easier to insert the needle into the patient and does not require any manipulation of the assembly 10 before use. Additionally, the orientation of the shield 50 and wings 20 and 22 provides a visual indication to the user of the orientation of the bevel end 14a of the needle 14.

Figure 3:
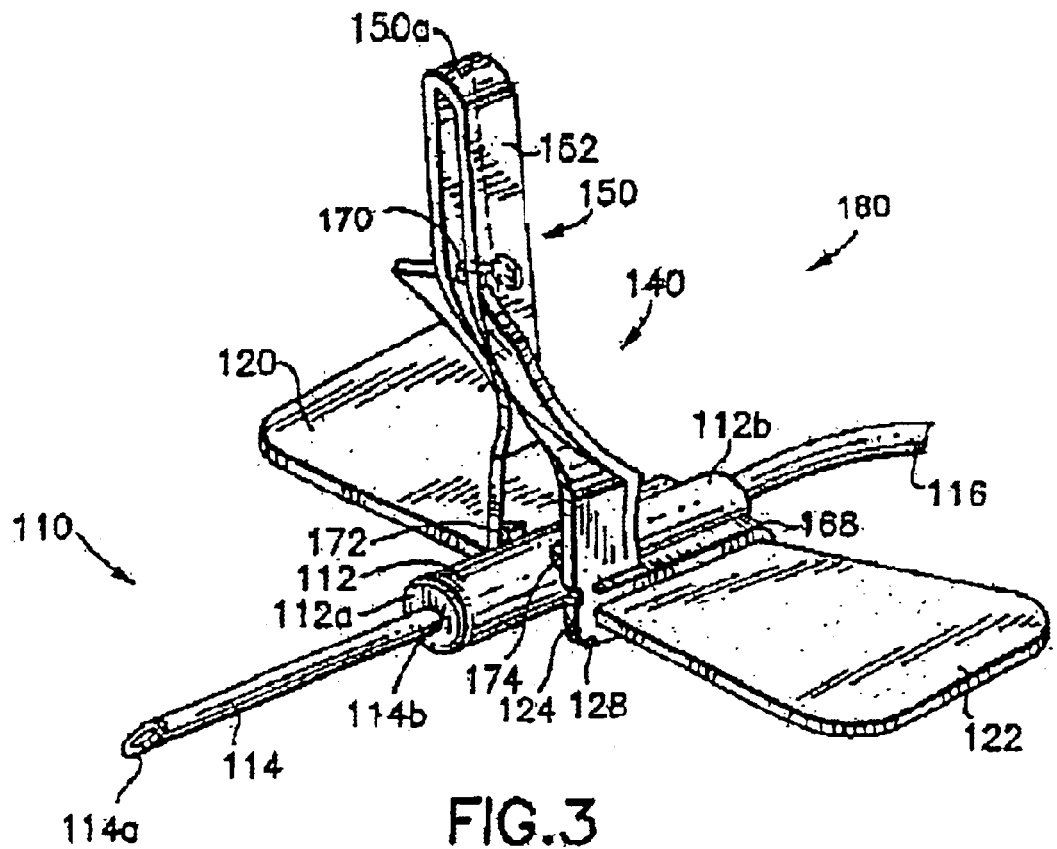
FIG. 3 is a perspective view of a further embodiment of the safety shield assembly of the present invention as connected to a blood infusion set shown in the open position.
Figure 4:
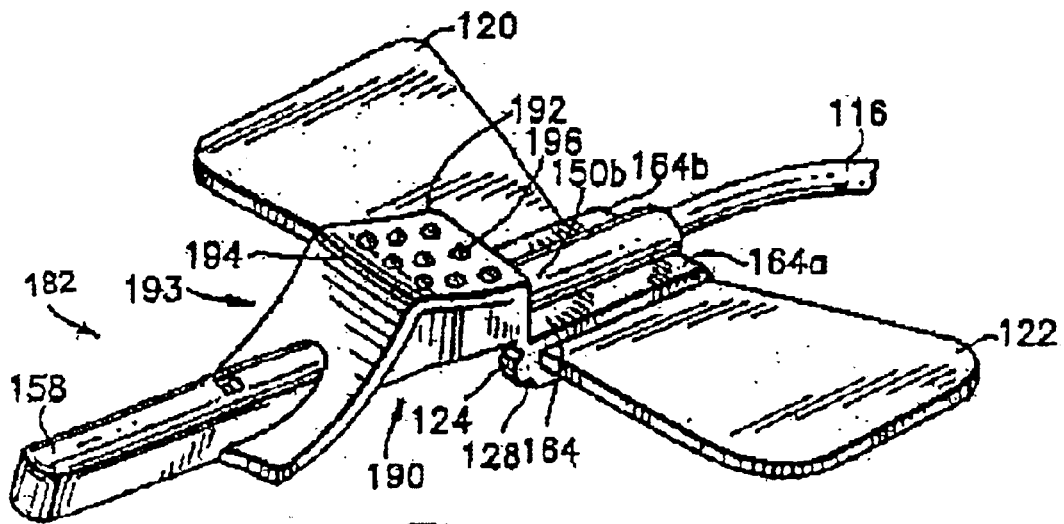
FIG. 4 is a perspective view of the inventive safety shield assembly of FIG. 3 shown in the forward locked position.

A further embodiment of the present invention is shown in FIGS. 3 and 4 wherein an alternate arrangement of the shield is shown. The infusion needle assembly is identical in both embodiments.

The needle assembly 110 of the present embodiment, as shown in FIGS. 3 and 4, includes many components which are substantially identical to the components of FIGS. 1 and 2. Accordingly, similar components performing similar functions will be numbered similarly to those components of FIGS. 1 and 2, except that 100 will be added to identify the components in FIGS. 3 and 4, i.e. 10 will be now labeled 110.

The shield assembly 140 in FIGS. 3 and 4 has its hinge axis 124 on the distal end 112a (or needle side) of the housing 112. In this embodiment, the proximal protrusions 172 and 174 engage the housing 112 on the distal end 112a of the housing 112. The distal protrusion 170 engages the needle 114 in an identical manner as in the first embodiment shown in FIGS. 1 and 2.

Safety shield assembly 140 is mounted to the infusion needle assembly 110 by clip 164. Clip 164 includes two spaced apart clip extenders 164a and 164b which surround wings 120 and 122 adjacent to the housing 112. The function of all the other aspects of the safety shield assembly 140 are identical.

The present invention further contemplates that a polymeric gel material (not shown) may be located in the recess area 60 of the shield 40 (FIG. 1) so that when the needle 14 enters the recess area, it will come to rest in the gel material. The gel material provides a way of minimizing exposure to the user to residual fluid on the needle by containing any residual fluid that may be on the needle.

The needle assembly may also include a removable distal cover (not shown) releasably mounted on the housing for covering the needle. The distal cover provides physical protection for the distal point and may serve as a barrier to passage of microorganisms until it is removed prior to use.

Additionally, a label (not shown) may also be applied to the assembled parts. The label may be applied in such as way that it is used to show use or tampering of parts and to ensure that the needle assembly is not reused.

Preferably, the shield and housing are moldable parts which can be mass produced as will be understood, from a variety of materials including, for example, polyethylene, polyvinyl chloride, polystyrene, and the like. Additionally, certain metals may be found to be useful for the shield and housing. Materials are selected which will provide the proper covering and support for the structure of the invention in its use, but which will provide also a degree of resiliency for the purposes of providing the cooperative movement relative to the cooperating abutments of the assembly.

The shield IV infusion or blood collection assembly of the present invention may be used in a manner similar to standard winged type assemblies. For instance, for IV infusion assemblies, the assembly of the present invention is connected to an IV apparatus and the needle placed in the patient. The safety shield is maintained about the hinge axis towards the proximal side of the assembly so that it does not interfere with the placement of the needle. The wings on either side of the assembly may be used to help position the needle in a desirable angle in the vein. Once the needle is removed, the shield is pivotally moved about the hinge axis toward the distal side of the needle until the shield reaches its permanently locked position. Desirably the shield assembly is moved with one hand, which leaves the user's other hand free.

Use of the present invention imposes little additional requirements on the practitioner in normal use of a needle assembly or IV infusion assembly. Except for moving the shield from the proximal position to the distal position, all other steps of the practitioner's tasks follow normal accepted practice.

The safety shield assembly of the present invention may be used in conjunction with a syringe assembly, a hypodermic needle, a needle assembly, a needle assembly with a needle holder, a blood collection set or other fluid handling devices. Preferably, the inventive assembly is an intravenous infusion assembly or blood collection assembly.

What is claimed is:

1. A shielded intravenous infusion or blood collection assembly comprising:

an elongate needle;

a length of tubing;

an elongate housing being supportingly interposed between said needle at a distal end and said tubing at a proximal end and in fluid communication therewith, said housing comprising a pair of oppositely directed outwardly extended wings;

a shield having a hinge with hinge axis about which said shield pivots, said shield being secured to said housing for pivotal movement about said hinge from an open position away from said needle to a closed position enclosing said needle, wherein said hinge axis is normal to a plane that bisects said wings; and mounting means for mounting said shield to said housing wherein said mounting means includes a clip positionable about said wings adjacent said housing for securing said shield to said housing, wherein said shield comprises a proximal end, a distal end, a pair of opposed shield sidewalls and a top surface thereby defining an elongated recess extending from said distal end to said proximal end for housing said needle therein when said shield is in said closed position;

wherein said shield sidewalls comprise at least one inwardly directed protrusion adjacent said distal end of said recess of said shield, said distal protrusion being configured so as to be deflectable by said needle when said needle enters said elongated recess and returnable to an undeflected position when said shield is in said closed position.

2. A shielded intravenous infusion or blood collection assembly comprising:

an elongate needle;

a length of tubing;

an elongate housing being supportingly interposed between said needle at a distal end and said tubing at a proximal end and in fluid communication therewith, said housing comprising a pair of oppositely directed outwardly extended wings;

a shield having a hinge with hinge axis about which said shield pivots, said shield being secured to said housing for pivotal movement about said hinge from an open position away from said needle to a closed position enclosing said needle, wherein said hinge axis is normal to a plane that bisects said wings; and mounting means for mounting said shield to said housing wherein said mounting means includes a clip positionable about said wings adjacent said housing for securing said shield to said housing;

wherein said shield comprises a proximal end, a distal end, a pair of opposed shield sidewalls and a top surface thereby defining an elongated recess extending from said distal end to said proximal end for housing said needle therein when said shield is in said closed position, wherein said shield comprises a top finger guide area including a first ramp that extends slightly in an upwardly slope from said proximal end of said shield to a shoulder.

3. The assembly of claim 2, wherein said first ramp includes a plurality of touch bumps.

4. A safety device for a winged needle assembly having a needle, tubing and a housing in mutual fluid communication, said device comprising:

a shield pivotally supportable to said housing for pivotal movement from an open position away from said needle to a closed position enclosing said needle, said shield being connected to said housing, wherein said shield comprises a proximal end, a distal end, a pair of opposed shield sidewalls and a top surface thereby defining an elongated recess extending from said distal end to said proximal end for housing said needle therein, mounting means for mounting said shield to said housing, wherein said mounting means includes a pair of outwardly extending wings and a pair of clip extensions positionable about said wings adjacent said housing for securing said shield to said housing; and a hinge interposed between said shield and mounting means, said shield having a hinge with a hinge axis about which said shield pivots, wherein said axis is normal to a plane that bisects said wings, wherein said shield sidewalls comprise at least one inwardly directed protrusion adjacent said distal end of said recess of said shield, said distal protrusion being configured so as to be deflectable by said needle when said needle enters said elongated recess and returnable to its undeflected position when said shield is in said closed position.

5. The assembly of claim 4, wherein said shield comprises a top finger guide area including a first ramp that extends slightly on an upwardly slope from said proximal end of said shield to a shoulder, wherein said first ramp includes a plurality of touch bumps.

* * * * *